US008939893B2

(12) United States Patent
Kato et al.

(10) Patent No.: US 8,939,893 B2
(45) Date of Patent: Jan. 27, 2015

(54) SIGNAL TRANSMISSION DEVICE AND ENDOSCOPE SYSTEM

(75) Inventors: Shuichi Kato, Tokyo (JP); Susumu Kawata, Tokyo (JP); Makoto Honda, Yokohama (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 328 days.

(21) Appl. No.: 13/361,661

(22) Filed: Jan. 30, 2012

(65) Prior Publication Data
US 2012/0197085 A1 Aug. 2, 2012

Related U.S. Application Data

(63) Continuation of application No. PCT/JP2010/062449, filed on Jul. 23, 2010.

(30) Foreign Application Priority Data

Jul. 30, 2009 (JP) ................................ 2009-178247

(51) Int. Cl.
*A61B 1/04* (2006.01)
*A61B 1/00* (2006.01)
*A61B 1/06* (2006.01)

(52) U.S. Cl.
CPC ............... *A61B 1/04* (2013.01); *A61B 1/00018* (2013.01); *A61B 1/00124* (2013.01)
USPC ............ 600/110; 600/109; 600/132; 600/160

(58) Field of Classification Search
USPC ............. 600/109, 110, 118, 132, 160; 348/65
See application file for complete search history.

(56) References Cited

U.S. PATENT DOCUMENTS

| 2003/0091118 A1 | 5/2003 | Lohr |
| 2005/0280509 A1 | 12/2005 | Tanaka et al. |
| 2006/0116550 A1 | 6/2006 | Noguchi et al. |
| 2006/0116552 A1 | 6/2006 | Noguchi et al. |

(Continued)

FOREIGN PATENT DOCUMENTS

| JP | 10-308728 A | 11/1998 |
| JP | 2004-511191 A | 4/2004 |

(Continued)

OTHER PUBLICATIONS

Japanese Notice of Allowance dated Sep. 3, 2013, issued in corresponding Japanese Patent Application No. 2009-178247 with English translation (6 pages).

(Continued)

*Primary Examiner* — Anhtuan T Nguyen
*Assistant Examiner* — William Chou
(74) *Attorney, Agent, or Firm* — Westerman, Hattori, Daniels & Adrian, LLP

(57) ABSTRACT

A signal transmission device includes a transmission unit, a first connection unit, a second connection unit, and a reception unit. The transmission unit sends a transmission signal. The first connection unit includes a first electrode electrically connected to the transmission unit. The second connection unit includes a second electrode that engages with the first connection unit, and, when engaged with the first connection unit, is statically coupled with the first electrode. The reception unit is electrically connected to the second electrode and receives the transmission signal.

4 Claims, 7 Drawing Sheets

(56) References Cited

U.S. PATENT DOCUMENTS

| | | |
|---|---|---|
| 2007/0078304 A1 | 4/2007 | Shimizu et al. |
| 2009/0058997 A1 | 3/2009 | Kato |

FOREIGN PATENT DOCUMENTS

| | | |
|---|---|---|
| JP | 2004-147052 A | 5/2004 |
| JP | 2006-5651 A | 1/2006 |
| JP | 2006-287052 A | 10/2006 |
| JP | 2007-97767 A | 4/2007 |
| JP | 2008-224936 A | 9/2008 |
| JP | 2009-56240 A | 3/2009 |
| JP | 2009-61032 A | 3/2009 |
| WO | 2005/077249 A1 | 8/2005 |
| WO | 2005/077250 A1 | 8/2005 |
| WO | 2009/035028 A1 | 3/2009 |

OTHER PUBLICATIONS

International Search Report of PCT/JP2010/062449, mailing date of Aug. 24, 2010.

SIGNAL TRANSMISSION DEVICE AND ENDOSCOPE SYSTEM

This application is a continuation application based on a PCT Patent Application No. PCT/JP2010/062449, filed Jul. 23, 2010, whose priority is claimed on Japanese Patent Application No. 2009-178247, filed in Jul. 30, 2009, the content of which is incorporated herein by reference.

BACKGROUND OF THE INVENTION

1. Field of the Invention

The present invention relates to a signal transmission device and an endoscope including the signal transmission device.

2. Description of Related Art

A static coupling method using static coupling of a pair of elements, such as that disclosed in, for example, Japanese Unexamined Patent Application, First Publication No. 2004-511191, is used for noncontact transmission of signals.

When a transmission unit and a reception unit are coupled in an AC (alternating current) manner as in a static coupling method, Manchester encoding, in which the strength level of each signal of a transmission signal is expressed as one of two types, an 'H' (or '1') signal and an 'L' (or '0') signal, and the numbers of 'H' signals and 'L' signals in each are made equal, is sometimes used to reduce intra-code interference by balancing the DC (direct current) levels of the transmission unit and the reception unit.

SUMMARY OF THE INVENTION

A signal transmission device according to a first aspect of the present invention includes a transmission unit that sends a transmission signal, a first connection unit having a first electrode electrically connected to the transmission unit, a second connection unit being connected to the first connection unit, the second connection unit having a second electrode, wherein the second electrode is statically coupled to the first electrode when the second connection unit engages with the first connection unit and a reception unit that is electrically connected to the second electrode and receives the transmission signal. The transmission unit expresses the transmission signal using the amount of change in the strength levels of successive signals with different strength levels, where one signal has three or more strength levels, and encodes it such that the average value of the strength levels of the successive signals is substantially constant, irrespective of the size of the transmission signal.

Preferably, the transmission unit may express the transmission signal using the amount of change in the strength levels of two successive signals with different the strength levels.

Preferably, the reception unit may identify the transmission signal by detecting a later signal of the two successive signals.

Preferably, the first connection unit may include a third electrode electrically connected to the transmission unit and, the second connection unit may include a fourth electrode that is electrically connected to the reception unit. The fourth electrode is statically coupled with the third electrode when the second connection unit is engaged with the first connection unit. The signal delivered by static coupling of the third electrode and the fourth electrode may be in reverse phase to that of the signal delivered by static coupling of the first electrode and the second electrode.

An endoscope system according to a second aspect of the present invention includes an endoscopic scope including an insertion part that is inserted into a living body and is provided with an observation means capable of observing a distal-end side, a living body exterior device provided outside the living body, and the signal transmission device according to described above. The endoscopic scope is provided with the transmission unit. The living body exterior device is provided with the reception unit. The first connection unit and the second connection unit are configured to be capable of connecting and disconnecting to/from each other.

DETAILED DESCRIPTION OF THE INVENTION

The embodiments of the present invention will be explained while referring to specific embodiments. Based on the description of the invention, various different embodiments may be able to be adopted, and the invention is not limited to the embodiments illustrated for the sake of explanation.

(First Embodiment)

A first embodiment of a signal transmission device according to the present invention will be explained with reference to FIGS. 1 to 5.

Figure 1:
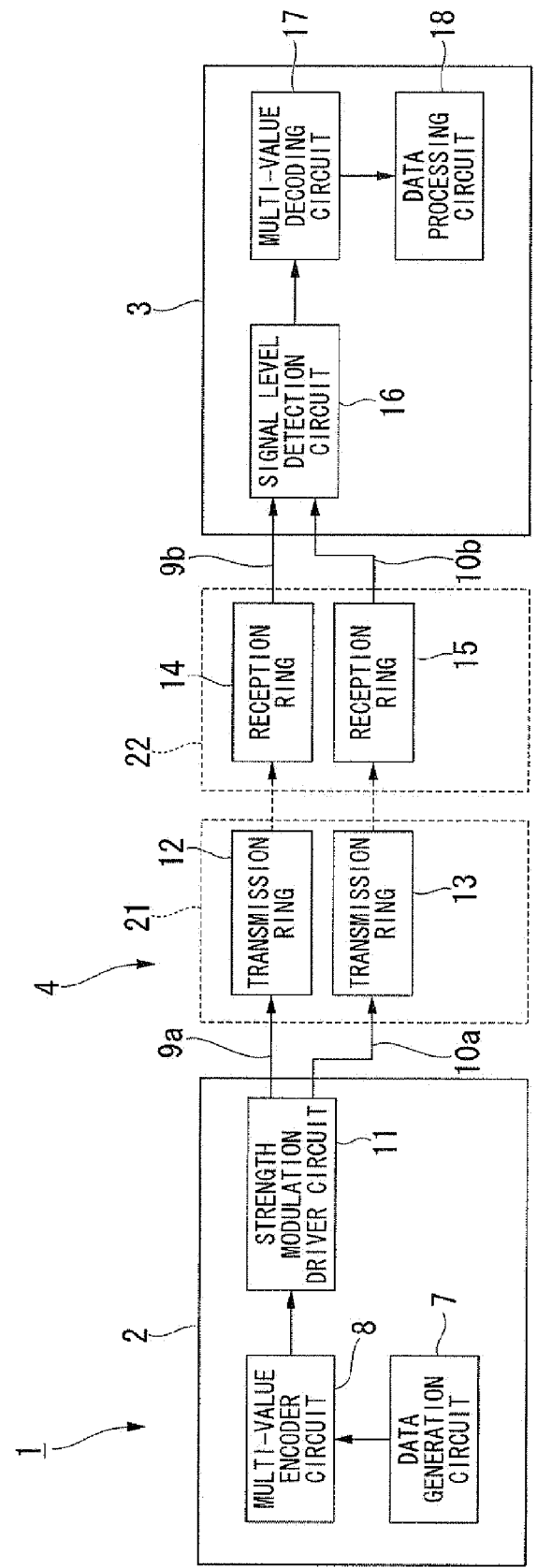
FIG. 1 A block diagram indicating the configuration of a signal transmission device according to a first embodiment of the present invention.

As shown in FIG. 1, a signal transmission device 1 of this embodiment includes a transmission unit 2 that transmits transmission data (transmission signal), a reception unit 3 that receives the transmission data, and a static coupling unit 4 that divides the transmission unit 2 side and the reception unit 3 side in a DC (direct current) manner and transmits the signal.

The transmission unit 2 includes a data generation circuit 7 that generates transmission data constituted by a multi-value signal described below, a multi-value encoder circuit 8 that modulates this transmission data to a signal having four types of strength level, and a strength-modulation driver circuit 11 that outputs the signal modulated by the multi-value encoder circuit 8 and the signal in a reverse phase to the encoded data to one end of each of transfer lines 9a and 10a.

The static coupling unit 4 includes a transmission ring (first electrode) 12 and a transmission ring (third electrode) 13, which are electrically connected to the strength-modulation driver circuit 11 by the transfer lines 9a and 10a respectively, and a reception ring (second electrode) 14 and a reception ring (fourth electrode) 15 that deliver signals by static coupling with the transmission rings 12 and 13 respectively.

Detailed shapes of a transmission-side connection unit (first connection unit) 21 and a reception-side connection unit (second connection unit) 22 that include the static coupling unit 4 will be explained later.

Encoded data output via the strength-modulation driver circuit 11 to one end of the transfer line 9a is delivered via the transmission ring 12 provided at the end other of the transfer line 9a to the reception ring 14. Similarly, encoded data output via the strength-modulation driver circuit 11 to one end of the transfer line 10a is delivered via the transmission ring 13 provided at the end other of the transfer line 10a to the reception ring 15.

The reception unit 3 includes a signal level detection circuit 16 that is electrically connected to the reception rings 14 and 15 and detects the type of strength level of each signal delivered to them, a multi-value decoder circuit 17 that demodulates encoded data from signals having four types of strength level, and a data processing circuit 18 that performs data processing to the demodulated transmission data.

Encoded data delivered to the reception ring 14 is delivered to the signal level detection circuit 16 by a transfer line 9b, one end of which connects to the reception ring 14. Similarly, reverse-phase data delivered to the reception ring 15 is delivered to the signal level detection circuit 16 by a transfer line 10b, one end of which connects to the reception ring 15.

At the signal level detection circuit 16, by taking the difference in strength levels of the delivered encoded data and the reverse-phase data, i.e. by using the differential signal, noise similarly contained in these two pieces of data can be removed.

In this embodiment, a multi-value decoder circuit 17 also functions as a clock reproduction circuit that reproduces a clock from the encoded data. The multi-value decoder circuit 17 then uses the reproduced clock to decode the transmission data from signals having four types of strength levels.

The decoded data is delivered to the data processing circuit 18 and processed.

Figure 2:
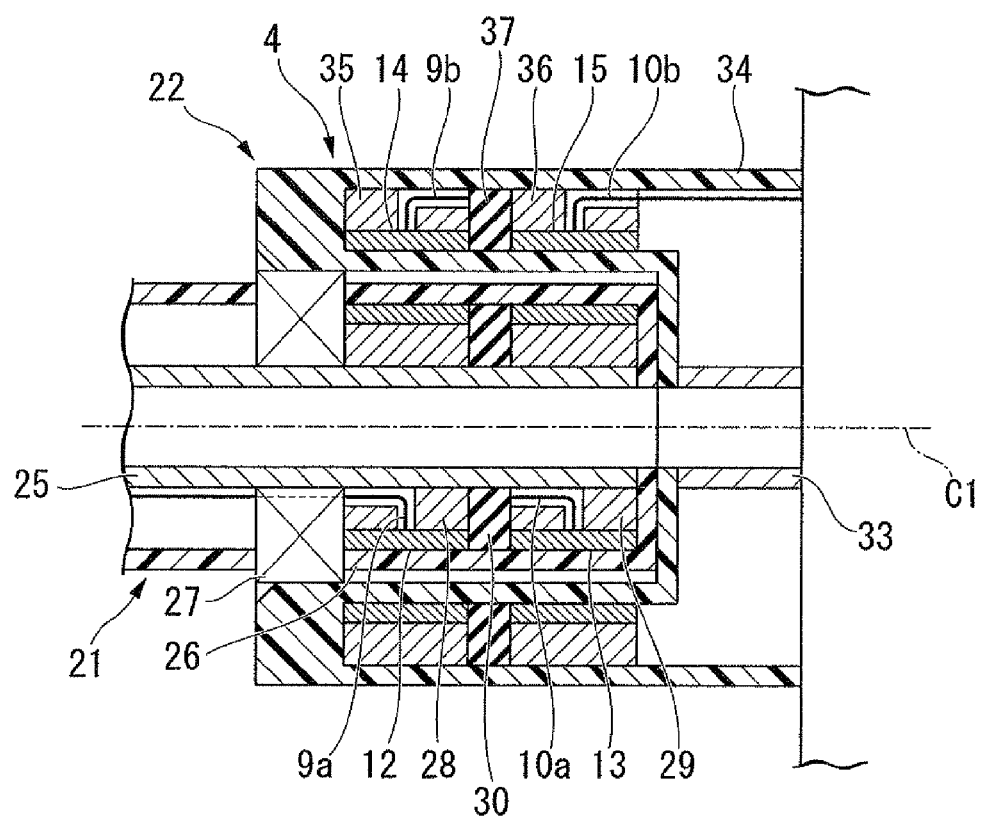
FIG. 2 A cross-sectional diagram of signal transmission device in a state where a reception side connection unit and a transmission side connection unit of the same are connected.

Subsequently, as shown in FIG. 2, the coupling unit 4, which includes the transmission-side connection unit 21 including the transmission ring 12 and the transmission ring 13, and the reception-side connection unit 22 including the reception ring 14 and the reception ring 15, will be explained.

The transmission-side connection unit 21 is formed in a substantially circular-column shape, and the reception-side connection unit 22 is formed in a substantially cylindrical shape such as to surround the outer peripheral face of the transmission-side connection unit 21. The transmission-side connection unit 21 is capable of being connected and disconnected to/from the reception-side connection unit 22. When the transmission-side connection unit 21 is connected to the reception-side connection unit 22, each is disposed on a common axis C1 concentrically.

The transmission-side connection unit 21 includes a transmission-side axis member 25 that is tubular in shape and is disposed such that its own axis matches the axis C1, the transmission rings 12 and 13 that are cylindrical in shape and are disposed such that their own axes each match the axis C1, a transmission-side covering member 26 made from a dielectric provided such as to cover the top face including the outer peripheral faces of the transmission rings 12 and 13, and a bearing 27 formed in a ring shape.

The transmission rings 12 and 13 are disposed such as to extend along the axis C1, and are respectively attached to the transmission-side axis member 25 via supporting members 28 and 29 made from a material having insulating properties. The transfer lines 9a and 10a connected to the transmission ring 12 and the transmission ring 13 are inserted into through-holes provided in the supporting members 28 and 29 and connected to the strength-modulation driver circuit 11.

A shielding member 30 is provided between the transmission ring 12 and the transmission ring 13 to block any electromagnetic effect between them.

The bearing 27 is formed such as to protrude slightly radially outward from the transmission-side covering member 26, and is in an exposed state. The outer peripheral face and inner peripheral face of the bearing 27 are arranged along the axis C1. The outer peripheral face is configured to being capable of rotate around the axis C1 with respect to the inner peripheral face in a state of reduced frictional force.

The reception-side connection unit 22 includes a reception-side axis member 33 that is tubular in shape and is disposed such that its own axis matches the axis C1, the reception rings 14 and 15 that are cylindrical in shape and are disposed such that their own axes each match the axis C1, and a reception-side covering member 34 made from a dielectric provided so as to cover the top face including the inner peripheral faces and outer peripheral faces of the reception rings 14 and 15.

The reception rings 14 and 15 are disposed so as to extend along the axis C1, and supporting members 35 and 36 made from a material having insulating properties are respectively attached, on the outer peripheral faces of the reception rings 14 and 15. The transfer lines 9b and 10b connected to the reception ring 14 and the reception ring 15 are inserted into through-holes provided in the supporting members 35 and 36 and connected to the signal level detection circuit 16.

A shielding member 37 is provided between the reception ring 14 and the reception ring 15 to block any electromagnetic effect between them.

With the axis of the reception-side connection unit 22 and the axis of the transmission-side connection unit 21 in a matched state, when the inner peripheral face of the reception-side covering member 34 is attached to the outer peripheral face of the bearing 27, the transmission-side connection unit 21 is engaged with and is connected to the reception-side connection unit 22.

By connecting in this manner, the transmission-side connection unit 21 is able to rotate around the axis C1 with respect to the reception-side connection unit 22; in addition, the reception ring 14 is disposed opposite the transmission ring 12, and the reception ring 15 is disposed opposite the transmission ring 13. The transmission ring 12 is disposed to being capable of be statically coupled with the reception ring 14, and the transmission ring 13 is disposed to being capable of statically coupled with the reception ring 15.

The operation of each part of the signal transmission device 1 of FIG. 1 will be explained using the timing chart of FIG. 3 and the flowchart of FIG. 4.

The data generation circuit 7 of the transmission unit 2 shown in FIG. 1 generates transmission data, for example, '0, 1, 2, 3, 0, . . . ' in decimal notation such as is shown in FIG. 3. When the transmission data is expressed as a signal including two strength levels, namely an 'H' signal and an 'L' signal, two signals including two strength levels are needed to express four types of signals '0' to '3' in decimal notation. The first and second signals of the two signals corresponding to '0' to '3' in decimal notation become the strength levels shown in decimal notation as shown in FIG. 3.

Figure 3:
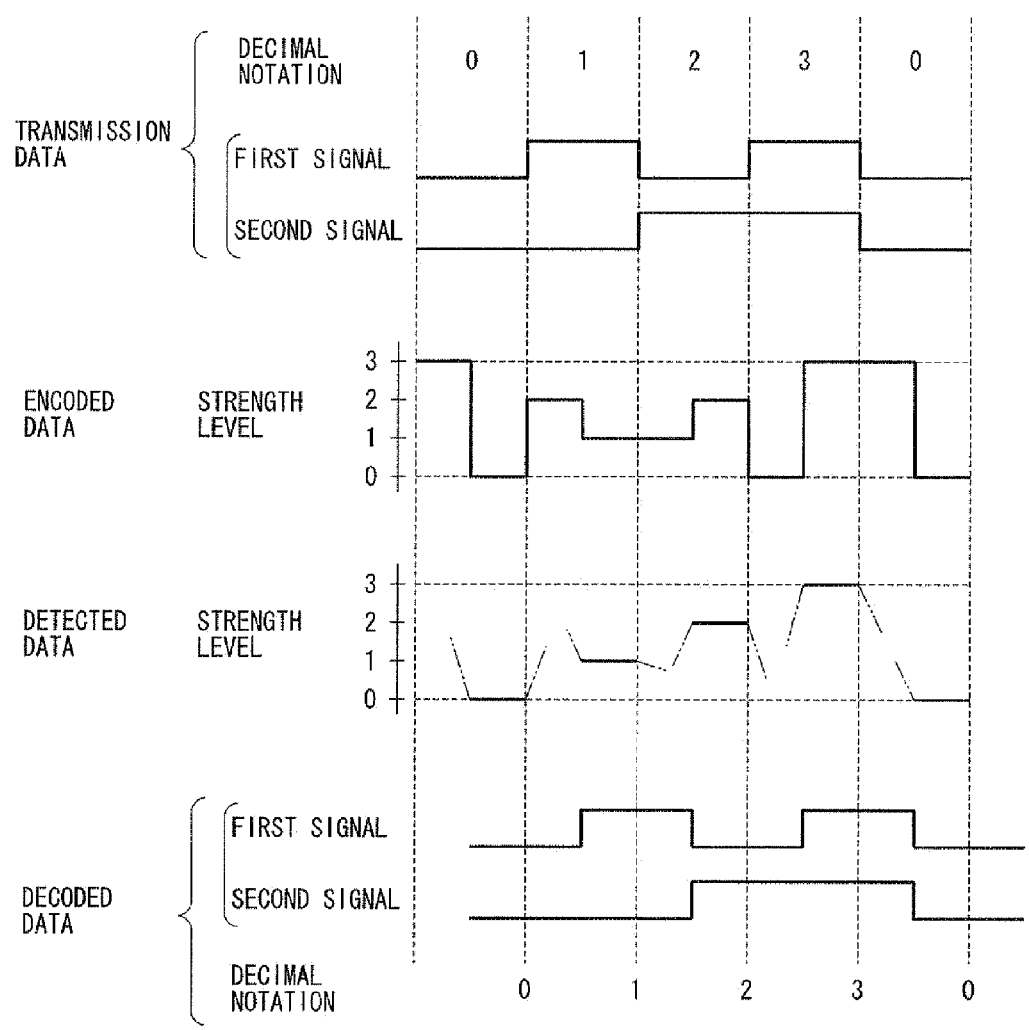
FIG. 3 A timing diagram of an operation of signal transmission in the signal transmission device.
Figure 4:
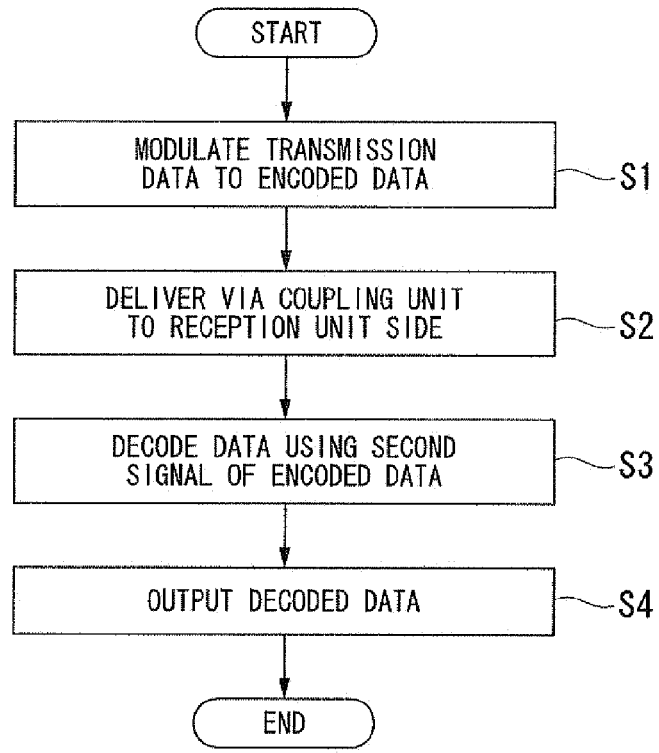
FIG. 4 A flowchart of operation of the signal transmission device.

When the transmission data expressed by two signals is input to the multi-value encoder circuit 8, as shown in Step S1 of FIG. 4, the multi-value encoder circuit 8 creates encoded data, in which each signal has four types of strength level, from the transmission data. FIG. 3 is an example of this encoded data.

The data in each signal is expressed with four types of strength level from level 0 to level 3. The four types of strength level are distinguished according to, for example, difference in the size of the voltage, with the differences between the strength levels (level 1 and level 0, level 2 and level 1, level 3 and level 2) being set such that they are mutually equal.

The encoded data expresses one value by the amount of change in the strength levels of the two successive signals which are grouped into That is, the strength level of the first signal and the strength level of the second signal (the later signal) are mutually different.

For example, of two successive signals, when the first signal is level 3 and the second signal is level 0, so that there is a difference of three strength levels between them, this is expressed in decimal notation as '0'. When the first signal is level 2 and the second signal is level 1, so that there is a difference of one strength level between them, this is expressed in decimal notation as '1', and so on.

Moreover, the transmission data is encoded such that the average value of the strength levels of the two successive signals is substantially constant (including constant), irrespective of the size of the transmission data expressed as '0' to '3' in decimal notation. Specifically, in encoded data that signifies '0' in decimal notation, the first signal is level 3 and the second signal is level 0, so that the average value of the strength levels of the two signals becomes a value between level 2 and level 1. Also, in encoded data that signifies '1' in decimal notation, the first signal is level 2 and the second signal is level 1, so that here too the average value of the strength levels of the two signals becomes a value between level 2 and level 1.

The strength-modulation driver circuit 11 creates data in reverse phase to the encoded data. As shown in FIG. 3, when the encoded data is level 3, level 0, level 2, level 1, . . . , the reverse-phase data becomes level 0, level 3, level 1, level 2, . . . .

As shown in Step S2, the encoded data and the reverse-phase data are delivered via the static coupling unit 4 to the reception unit 3 side.

FIG. 3 shows an example of a differential signal (hereinafter abbreviated as 'detected data') based on the encoded data and the reverse-phase data received by the reception rings 14 and 15 and detected by the signal level detection circuit 16. Since the strength level of the second signal of the two successive signals is different from the strength level of the first signal, as indicated by the solid line in FIG. 3, attenuation of the strength level of the second signal is suppressed. In contrast, the first signal suffers attenuation due to the strength level of the signal (the second signal) before it, and there is a possibility that its strength level may be difficult to be detected.

Figure 5:
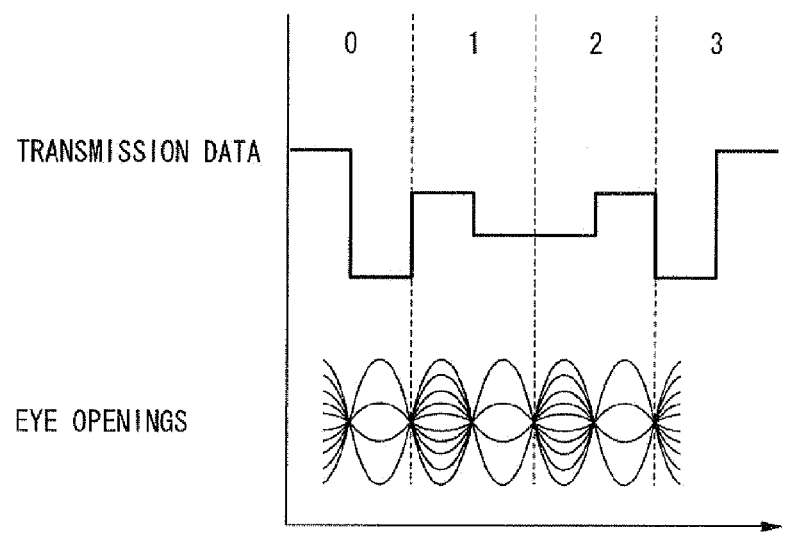
FIG. 5 An example of a graph of eye openings in signal transmission via a coupling unit of the signal transmission device.

Consequently, a graph of eye openings indicating the quality characteristics of the signals transmitted via the static coupling unit 4 becomes like, for example, the one shown in FIG. 5. While an eye opens in correspondence with the second signal, no eye opens in correspondence with the first signal. This graph reveals that it is possible to reliably detect and determine the strength level of the second signal of two successive signals expressing one value.

In a case where, for example, the transmission data goes from '1' to '2' in decimal notation, the second signal for '1' and the first signal for '2' will both be at level 1. In this case, there are successive signals with the same strength level, and the strength level of the first signal for '2' attenuates greatly.

The detected data is input to the multi-value decoder circuit 17, where a clock reproduction process is performed. As shown in Step S3, the multi-value decoder circuit 17 then uses this reproduced clock to perform a decoding process, with two successive signals of detected data as the unit of processing, so as to detect only the strength level of the second signal, whereby it identifies the one value and creates decoded data shown in FIG. 3.

As shown in Step S4, the decoded data created by the multi-value decoder circuit 17 is delivered to the data processing circuit 18, which performs a signal process to the decoded data.

Thus, according to the signal transmission device 1 of the first embodiment of the present invention, by making the transmission-side connection unit 21 engage with the reception-side connection unit 22, the transmission ring 12 of the transmission-side connection unit 21 and the reception ring 14 of the reception-side connection unit 22 become statically coupled. To the transmission ring 12, the transmission unit 2 sends successive signals of different strength levels, one signal having four types of strength level, the signals being encoded so as to express a transmission signal using the amount of change in the strength level. Therefore, by making the strength levels of successive signals different, it is possible to suppress attenuation of the strength level of the signal delivered to the reception ring 14 due to static coupling.

Moreover, since the transmission unit 2 encodes the data such that the average value of the strength levels of the successive signals is substantially constant, irrespective of the size of the transmission signal, even if the transmission signal is coded as a multi-value signal with four types of strength level, the DC level of the signal can be stabilized.

Furthermore, since the signal whose strength level is detected is the second of two successive signals, attenuation of the strength level due to successive signals with equal strength levels is suppressed, and the strength level of the signal can be reliably detected.

Furthermore, by making the transmission-side connection unit 21 engage with the reception-side connection unit 22, the transmission ring 12 is statically coupled with the reception ring 14, and the transmission ring 13 is statically coupled with the reception ring 15. The static coupling between the transmission ring 12 and the reception ring 14 delivers encoded data from the transmission unit 2 to the reception unit 3, and the static coupling between the transmission ring 13 and the reception ring 15 delivers reverse-phase data of the encoded data from the transmission unit 2 to the reception unit 3.

Therefore, by detecting the difference in the strength levels of both pieces of data, it is possible to reduce common noise contained in them, and to more reliably detect the data delivered by static coupling.

In this embodiment, the transmission unit 2 includes the data generation circuit 7. However, the configuration may be adopted that where the transmission unit 2 does not include the data generation circuit 7, and the transmission data is input to the multi-value encoder circuit 8 from the outside. Also, in this embodiment, the reception unit 3 includes the data processing circuit 18. However, the configuration can be one where the reception unit 3 does not include the data processing circuit 18, and data decoded by the multi-value decoder circuit 17 is output to the outside.

(Second Embodiment)

Subsequently, a second embodiment of the present invention will be explained. Like parts to those of the embodiment described above are designated with like reference numerals and are not repetitiously explained; only points of difference will be explained.

Figure 6:
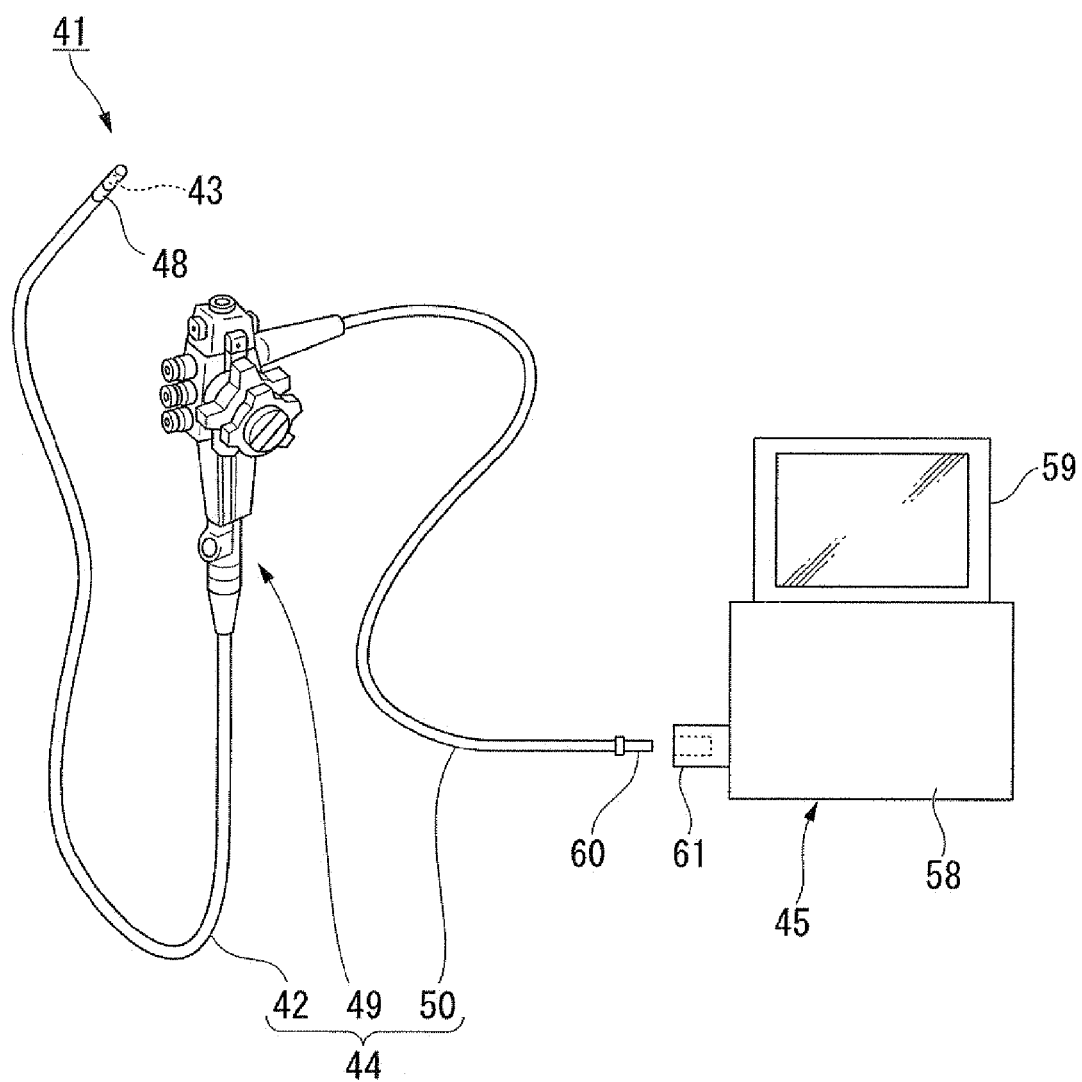
FIG. 6 A diagram of the overall configuration of an endoscope system according to a second embodiment of the present invention.
Figure 7:
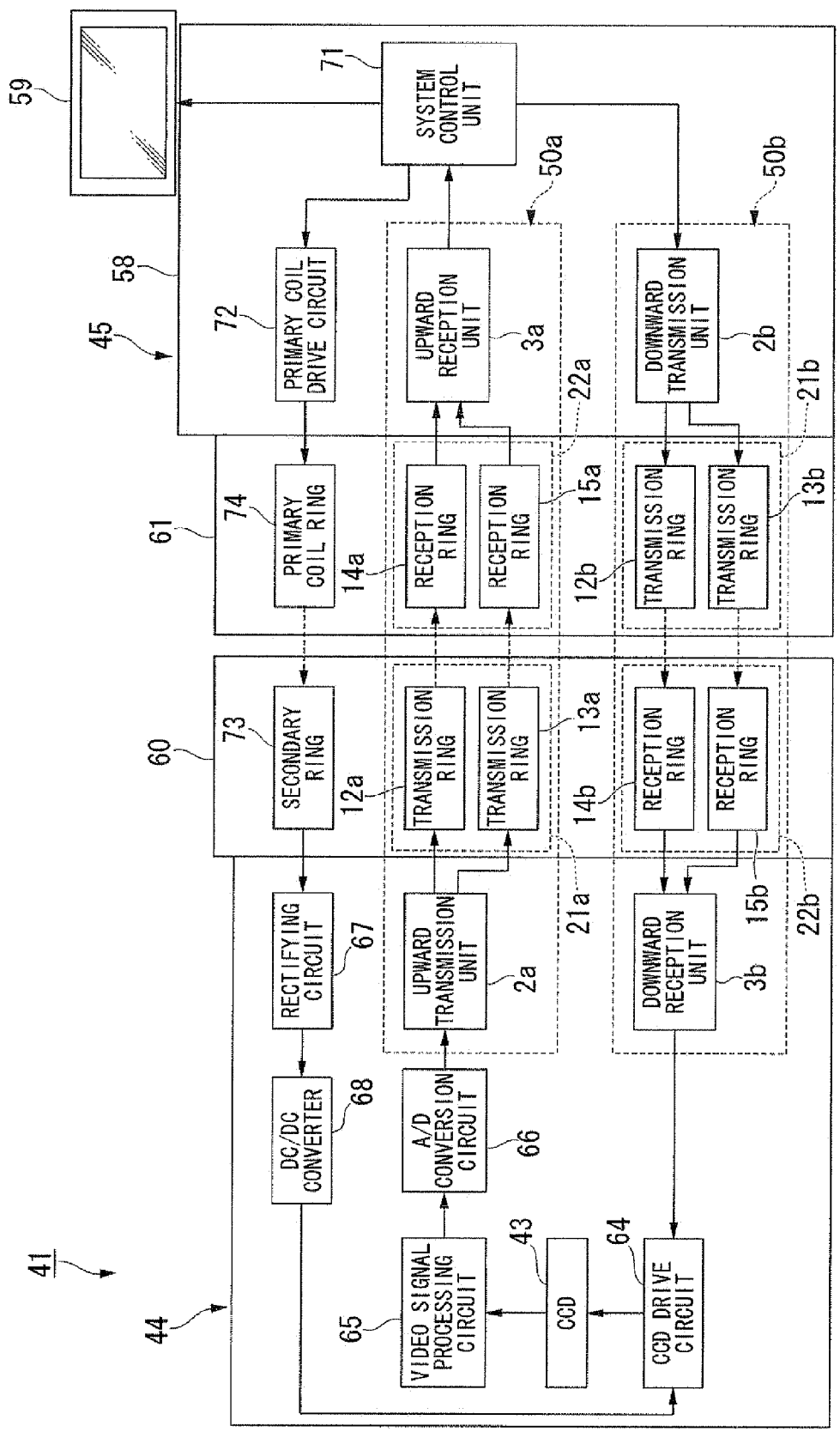
FIG. 7 A block diagram indicating the configuration of the endoscope system.

As shown in FIGS. 6 and 7, an endoscope system 41 is a device for inserting an insertion part 42 into a living body, and observing the inside of the living body.

The endoscope system 41 of this embodiment includes an endoscopic scope 44 including an insertion part 42 that is inserted into a living body and is provided with a CCD (observation means) 43 capable of observing a distal-end side, a living body exterior device 45 provided outside the living body, and the signal transmission devices 50a and 50b described above, which are built into the endoscopic scope 44 and the living body exterior device 45.

The signal transmission devices 50a and 50b of this embodiment are not provided with the data generation circuit 7 and the data processing circuit 18 of the embodiment described above; instead, transmission data from the outside is input to the transmission unit, and the reception unit outputs decoded data to the outside.

Like parts of the signal transmission devices 50a and 50b to those of the embodiment described above are designated with like reference numerals followed by the letter 'a' or 'b' to identify them, and are not repetitiously explained.

As shown in FIG. 6, the endoscopic scope 44 includes the insertion part 42 mentioned above, which is made from a flexible material and includes a bend part 48 on its distal-end side, an operation part 49 attached to the proximal-end side of the insertion part 42 and including an angle knob or the like for controlling the bending of the bend part 48, and a universal cord 50 for connecting the operation part 49 to the living body exterior device 45.

At the distal-end part of the insertion part 42, i.e. the distal-end side of the bend part 48, an illuminating means which are not illustrated such as a light-gathering optical system for illuminating the distal-end side with illuminating light that has been led along a living body outer-side light guide 84 and a scope-side light guide 79 described below, and the CCD 43 are provided.

The living body exterior device 45 includes a main unit 58 as its base, and a display unit 59 that displays a video signal from the CCD 43. A scope-side connection part 60 and a living body outer-side connection part 61 which is capable of connecting and is connecting to/from each other are provided between the proximal-end part of the universal cord 50 and the main unit 58.

In this embodiment, as described in detail below, data can be delivered from the endoscopic scope 44 to the living body exterior device 45 (upward) and from the living body exterior device 45 to the endoscopic scope 44 (downward).

In this embodiment, since the scope-side connection part 60 and the living body outer-side connection part 61 are provided between the proximal-end part of the universal cord 50 and the main unit 58, the universal cord 50 constitutes the endoscopic scope 44. However, when the scope-side connection part and the living body outer-side connection part are provided between the proximal-end part of the universal cord 50 and the operation part 49, the universal cord constitutes the living body exterior device 45.

That is, the endoscopic scope is the part on the insertion part 42 side of the section divided by the scope-side connection part and the living body outer-side connection part, while the living body exterior device is the part on the main unit 58 side.

As shown in FIG. 7, the endoscopic scope 44 includes a CCD driver circuit 64 that controls the drive status of the CCD 43, a video signal processing circuit 65 that processes image data (video signals) and the like captured by the CCD 43, an A/D conversion circuit 66 that converts an analog signal obtained by the video signal processing circuit 65 to a digital signal, a rectifying circuit 67 that converts alternating current to direct current, and a DC/DC converter 68 that adjusts the voltage of the direct current.

The endoscopic scope 44 further includes an upward transmission unit 2a of the signal transmission device 50a, and a downward reception unit 3b of the signal transmission device 50b.

The main unit 58 includes a system control unit 71 that controls the endoscopic scope 44 and the living body exterior device 45, and processes video signals, a primary coil driver circuit 72 that controls the drive status of a primary coil ring 74 described below, an upward reception unit 3a of the signal transmission device 50a, and a downward transmission unit 2b of the signal transmission device 50b.

The scope-side connection part 60 includes a secondary coil ring 73 which electric power is supplied to, a transmission ring (first electrode) 12a and a transmission ring (third electrode) 13a of the signal transmission device 50a, and a reception ring (second electrode) 14b and a reception ring (fourth electrode) 15b of the signal transmission device 50b.

The living body outer-side connection part 61 includes a primary coil ring 74 which supplies electric power, a reception ring (second electrode) 14a and a reception ring (fourth electrode) 15a of the signal transmission device 50a, and a transmission ring (first electrode) 12b and a transmission ring (third electrode) 13b of the signal transmission device 50b.

Subsequently, configurations of the scope-side connection part 60 and the living body outer-side connection part 61 will be explained.

Figure 8:
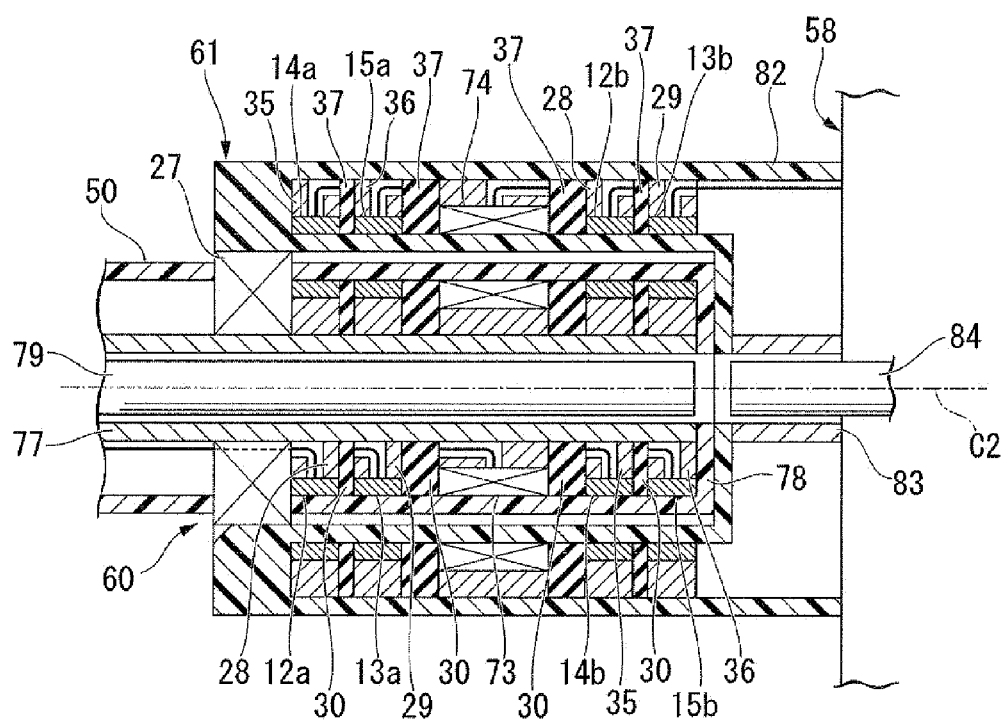
FIG. 8 A cross-sectional diagram of the endoscope system in a state where a living-body outside connection part and a scope-side connection part of the same are connected.

As shown in FIG. 8, the scope-side connection part 60 is formed in a substantially circular-column shape, and the living body outer-side connection part 61 is formed in a substantially cylindrical shape such as to surround the outer peripheral face of the scope-side connection part 60. When the scope-side connection part 60 is connected to the living body outer-side connection part 61, each is disposed on a common axis C2 concentrically.

The reception ring 15b, the reception ring 14b, the secondary coil ring 73, the transmission ring 13a, and the transmission ring 12a are attached in that order via supporting members 28 29 35 36 etc made from material with insulating properties, on the same axis from the proximal-end part side of a tubular scope-side axis member 77 toward the center part side, to the proximal-end part of the scope-side axis member 77. Shielding members 30 are provided between the reception ring 15b and the reception ring 14b, between the reception ring 14b and the secondary ring 73, between the secondary ring 73 and the transmission ring 13a, and between the transmission ring 13a and the transmission ring 12a, to block any electromagnetic effects between them.

The top face, including the outer peripheral faces of the reception rings 15b and 14b, the secondary ring 73, and the transmission rings 13a and 12a, is covered by a scope-side covering member 78 made from a dielectric.

Furthermore, a scope-side light guide 79 is inserted into the scope-side axis member 77, and leads illuminating light to an unillustrated illuminating means.

In the living body outer-side connection part 61, the reception ring 14a, the reception ring 15a, the primary ring 74, the transmission ring 12b, and the transmission ring 13b are provided in that order on the same axis leading towards the main unit 58 side. Shielding members 37 are provided between the reception ring 14a and the reception ring 15a, between the reception ring 15a and the primary coil ring 74, between the primary coil ring 74 and the transmission ring 12b, and between the transmission ring 12b and the transmission ring 13b, to block any electromagnetic effects between them.

The top face, including the outer peripheral faces of the reception rings 14a and 15a, the primary coil ring 74, and the transmission rings 12b and 13b, is covered by a living body outer-side covering member 82 made from a dielectric.

Furthermore, a living body outer-side light guide 84 is inserted into a tubular living body outer-side axis member 83, and leads illuminating light generated by an unillustrated illuminating means provided inside the main unit 58.

With the axis of the scope-side connection part 60 and the axis of the living body outer-side connection part 61 in a matched state, when the inner peripheral face of the living body outer-side covering member 82 is attached to the outer peripheral face of the bearing 27, the scope-side connection part 60 is engaged with and is connected to the living body outer-side connection part 61.

By connecting in this manner, the scope-side connection part 60 is able to rotate around the axis C2 with respect to the living body outer-side connection part 61; in addition, the transmission ring 12a is disposed opposite the reception ring 14a, the transmission ring 13a is disposed opposite the transmission ring reception 15a, the secondary ring 73 is disposed opposite the primary coil ring 74, the reception ring 14b is disposed opposite the transmission ring 12b, and the reception ring 15b is disposed opposite the reception ring transmission 13b.

At this time, the side face of the scope-side light guide 79 and the side face of the living body outer-side light guide 84 are also disposed opposite each other, enabling illuminating light to be delivered from the living body outer-side light guide 84 side to the scope-side light guide 79.

Thus, the scope-side connection part 60 is provided with a first connection part 21a including a first electrode in the signal transmission device 50a, and a second connection part 22b including a second electrode in the signal transmission device 50b. The living body outer-side connection part 61 is provided with a second connection part 22a including a second electrode in the signal transmission device 50a, and a first connection part 21b including a first electrode in the signal transmission device 50b.

Subsequently, a step for delivering data and electrical power from the living body exterior device 45 to the endoscopic scope 44 (downward direction) will be explained.

As shown in FIG. 7, the system control unit 71 is connected to each of the downward transmission unit 2b, the upward reception unit 3a, the primary coil driver circuit 72, and the display unit 59.

When the system control unit 71 sends a signal for controlling the CCD 43 to the downward transmission unit 2b, the downward transmission unit 2b encodes the control signal, and creates encoded data and data in a reverse phase of the encoded data. These pieces of data are delivered by static coupling between the transmission ring 12b and the reception ring 14b, and between the transmission ring 13b and the reception ring 15b, and are decoded in the downward reception unit 3b.

The decoded control signal is delivered to the CCD driver circuit 64 connected to the downward reception unit 3b. Based on this control signal, the CCD driver circuit 64 controls the CCD 43 that itself is connected to.

When the system control unit 71 sends a control signal to the primary coil driver circuit 72, a predetermined AC current is supplied to the primary coil ring 74 connected to the primary coil driver circuit 72. Due to mutual induction between the primary coil ring 74 and the secondary ring 73, the AC current flows to the secondary ring 73. This AC current is sent to the rectifying circuit 67 connected to the secondary ring 73, where it is converted to DC current. The voltage of the converted DC current is adjusted by the DC/DC converter 68 connected to the rectifying circuit 67, and the DC current is then supplied to the CCD driver circuit 64 and the like.

Subsequently, a step for delivering a signal from the endoscopic scope 44 to the living body exterior device 45 (upward direction) will be explained.

A video signal captured by the CCD 43 is delivered to the video signal processing circuit 65 connected to the CCD 43, where it is processed to create an analog signal. This analog signal is converted to a digital signal by the A/D conversion circuit 66 connected to the video signal processing circuit 65. The converted digital signal is then delivered to the upward transmission unit 2a connected to the A/D conversion circuit 66.

The video signal delivered to the upward transmission unit 2a is encoded, and encoded data and data in a reverse phase to this encoded data are created. These pieces of data are delivered by static coupling between the transmission ring 12a and the reception ring 14a, and between the transmission ring 13a and the reception ring 15a, and are decoded by the upward reception unit 3a.

The decoded video signal is delivered from the upward reception unit 3a to the system control unit 71, where it is processed before being sent to the display unit 59, where it is displayed.

Thus, according to the endoscope system 41 of the second embodiment of the present invention, the endoscopic scope 44 is provided with the upward transmission unit 2a of the signal transmission device 50a, and the downward reception unit 3b of the signal transmission device 50b, the living body exterior device 45 is provided with the upward reception unit 3a of the signal transmission device 50a, and the downward transmission unit 2b of the signal transmission device 50b. By connecting the scope-side connection part 60 to the living body outer-side connection part 61, the transmission ring 12a and the reception ring 14a, and the reception ring 14b and the transmission ring 12b, are respectively disposed opposite each other and are statically coupled.

Therefore, a signal with a stabilized DC level can be sent from the upward transmission unit 2a to the upward reception unit 3a, and from the downward transmission unit 2b to the downward reception unit 3b.

Generally, fluid and the like from the living body sticks to the endoscopic scope 44. Consequently, by separating the scope-side connection part 60 and the living body outer-side connection part 61 and releasing the living body exterior device 45 and the endoscopic scope 44, the workability when cleaning only the endoscopic scope 44 can be enhanced.

Moreover, by covering the surface of the reception rings 15b, 14b, the secondary coil ring 73, the transmission rings 13a and 12a with the scope-side covering member 78, it is possible to suppress corrosion of the internal components such as the electrodes during cleaning.

Incidentally, in this embodiment, the signal transmission device is used in delivering transmission data in both directions between the endoscopic scope 44 and the living body exterior device 45. However, the signal transmission device can acceptably be used in, for example, delivering data only from the endoscopic scope 44 to the living body exterior device 45.

Furthermore, in this embodiment, instead of the primary coil driver circuit 72, the primary coil ring 74, and the secondary coil ring 73, the endoscopic scope 44 can be provided with a battery or the like, and this battery can supply power to the CCD driver circuit 64 etc.

While a first embodiment and a second embodiment of the present invention have been described in detail with reference to the drawings, the specific configuration is not limited to these embodiments, and includes modifications and the like that do not depart from the main points of the invention.

For example, in the first embodiment and the second embodiment described above, the multi-value encoder circuit 8 modulated the transmission data to a signal where every signal has four types of strength level. However, the number of types of strength levels of each signal need only be three or more. Four types, eight types, or sixteen types of strength level are preferable.

Furthermore, in the first embodiment and the second embodiment described above, a transmission ring as one electrode and a transmission ring as a second electrode were disposed such that they extend along the axis. However, the first electrode and the second electrode can be formed into plates, and disposed such that they intersect the axis.

Furthermore, in the first embodiment described above, it is acceptable not to use data in the reverse phase of the encoded data and to deliver only encoded data, and thus not to provide the transmission ring 13 and the reception ring 15. Similarly, in the second embodiment, it is acceptable to deliver only encoded data, and thus not to provide the transmission rings 13a and 13b and the reception rings 15a and 15b.

Furthermore, in the first embodiment and the second embodiment described above, the configuration can be one where, when there is low attenuation in the strength level of the signal, the reception unit identifies the one value with the strength level of the first of two successive signals.

Furthermore, in the first embodiment and the second embodiment described above, the configuration can be one where three or more successive signals express one value. In this case, two adjacent signals need only have different strength levels.

What is claimed is:

1. An endoscope system comprising:
    an endoscopic scope including an insertion part that is inserted into a living body and is provided with an observation means capable of observing a distal-end side;
    a living body exterior device provided outside the living body; and
    the signal transmission device, the signal transmission device comprises:
    a transmission unit comprising a multi-value encoder circuit converting a transmission signal to an encoded data each of which has n types of strength level, and a strength modulation driver circuit creating a reversed data which has reverse phase to the encoded data;
    a first connection unit having a first electrode electrically connected to the transmission unit;
    a second connection unit being connected to the first connection unit, the second connection unit having a second electrode, wherein the second electrode is statically coupled to the first electrode when the second connection unit engages with the first connection unit; and
    a reception unit being electrically connected to the second electrode, the reception unit receiving the encoded data and the reversed data via the first connection unit and the second connection unit, and comprising a multi-value decoder circuit creating a decoded data using the encoded data and the reversed data, wherein
    the n is natural number larger than 2,
    the encoded data and the reversed data are grouped into successive signals, and
    the transmission unit transmits the successive signals and data is encoded such that the average value of the strength levels of the successive signals is substantially constant, irrespective of the size of the transmission signal, and wherein
    the transmission unit being provided in the endoscopic scope;
    the reception unit being provided in the living body exterior device;
    and the first connection unit and the second connection unit are configured to be capable of connecting and disconnecting to/from each other.

2. The endoscope system according to claim 1, wherein the transmission unit expresses the transmission signal using the amount of change in the strength levels of two successive signals with different the strength levels.

3. The endoscope system according to claim 2, wherein the reception unit identifies the transmission signal by detecting a later signal of the two successive signals.

4. The endoscope system according to claim 1, wherein the reception unit further comprises a signal level detection circuit connected between the second electrode and the multi-value decoder circuit,
    the signal level detection circuit takes the difference in strength levels of the encoded data and the reversed data,
    the first connection unit includes a third electrode electrically connected to the transmission unit;
    the second connection unit includes a fourth electrode that is electrically connected to the signal level detection circuit, and, when the second connection unit is engaged with the first connection unit, is statically coupled with the third electrode; and
    the transmission signal delivered by static coupling of the third electrode and the fourth electrode is in reverse phase to that of the transmission signal delivered by static coupling of the first electrode and the second electrode.

* * * * *